United States Patent
Filliers et al.

(10) Patent No.: US 6,844,439 B2
(45) Date of Patent: Jan. 18, 2005

(54) PROCESS FOR THE PREPARATION OF IMIDAZOLE COMPOUNDS

(75) Inventors: Walter Ferdinand Maria Filliers, Beerse (BE); Rudy Laurent Maria Broeckx, Beerse (BE); Stefan Marcel Herman Leurs, Beerse (BE)

(73) Assignee: Jansen Pharmaceutica, NV, Keefse (BE)

( * ) Notice: Subject to any disclaimer, the term of this patent is extended or adjusted under 35 U.S.C. 154(b) by 0 days.

(21) Appl. No.: 10/471,215

(22) PCT Filed: Mar. 5, 2002

(86) PCT No.: PCT/EP02/02459

§ 371 (c)(1),
(2), (4) Date: Sep. 8, 2003

(87) PCT Pub. No.: WO02/072574

PCT Pub. Date: Sep. 19, 2002

(65) Prior Publication Data

US 2004/0138256 A1 Jul. 15, 2004

(30) Foreign Application Priority Data

Mar. 12, 2001 (EP) ............................................. 01200928

(51) Int. Cl.⁷ ...................... C07D 215/16; C07D 215/38
(52) U.S. Cl. ...................... 546/154; 546/155; 546/157; 546/158
(58) Field of Search ................................. 546/154, 155, 546/157, 158; 514/312

(56) References Cited

U.S. PATENT DOCUMENTS 6,037,350 A * 3/2000 Venet et al. ................. 514/312
6,150,377 A * 11/2000 Lyssikatos et al. ......... 514/312
6,169,096 B1 * 1/2001 Venet et al. ................. 514/312

FOREIGN PATENT DOCUMENTS

| WO | WO 97/16443 A1 | 5/1997 |
| WO | WO 97/21701 A1 | 6/1997 |
| WO | WO 98/40383 A1 | 9/1998 |
| WO | WO 98/49157 A1 | 11/1998 |
| WO | WO 00/12498 A1 | 3/2000 |
| WO | WO 00/12499 A1 | 3/2000 |

OTHER PUBLICATIONS

Shapiro, et al., "Synthesis of 2,5–Dilithio–1–Methylimidazole," *Tetrahedron Letters*, 1993, 3401–3404, vol. 34, No. 21.

Shapiro, et al., "Carboxylate Protection for the Synthesis of 4,5–Disubstituted 1–Methylimidazoles," *J. Org. Chem.*, 1994, 5524–5526, vol. 59.

* cited by examiner

*Primary Examiner*—D. Margaret Seaman
(74) *Attorney, Agent, or Firm*—Alana G. Kriegsman

(57) ABSTRACT

A process for the preparation of 4-(3-chlorophenyl)-6-[(4-chlorophenyl)hydroxy(1-methyl-1H-imidazol-5-yl)methyl]-1-methyl-2(1H)-quinolinone which comprises reacting 6-(4-chlorobenzoyl)-4-(3-chlorophenyl)-1-methyl-2(1H)-quinolinone with a $C_{6-8}$alkyllithium compound, 1-methylimidazole and a tri($C_{4-6}$alkyl)silyl halide to obtain better yields of the above product.

10 Claims, No Drawings

PROCESS FOR THE PREPARATION OF IMIDAZOLE COMPOUNDS

CROSS REFERENCE TO RELATED APPLICATIONS

This application is the national stage of Application No. PCT/EP02/02459, filed Mar. 5, 2002, which application claims priority from European Patent Application No. 01200928.8 filed Mar. 12, 2001.

The present invention relates to the preparation of 5-substituted imidazole compounds which have farnesyl tranferase inhibitory activity and which are also useful as intermediates for the preparation of other imidazole compounds having such activity.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p2^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

In WO 97/16443, WO 97/21701, WO 98/40383 and WO 98/49157, there are described 2-quinolone derivatives which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolone compounds having farnesyl transferase inhibiting activity are described in WO 00/12498, 00/12499 and 00/47574. A particular compound described in the above-mentioned WO 97/21701, namely (R)-(+)-6-[amino(4-chlorophenyl)(1-methyl-1H-imidazol-5-yl)methyl]-4-(3-chlorophenyl)-1-methyl-2(1H) quinolinone, has been found to have very potent activity against neoplastic diseases and is currently the subject of clinical trials to determine the extent of its therapeutic effect against various cancers. The absolute stereochemical configuration of the compound was not determined in the experiments described in the above-mentioned patent specification, but the compound was identified by the prefix "(B)" to indicate that it was the second compound isolated from column chromatography. The compound thus obtained has been found to have the (R)-(+)-configuration. This compound, which will be referred to below by its published code number R115777, has the following formula (I):

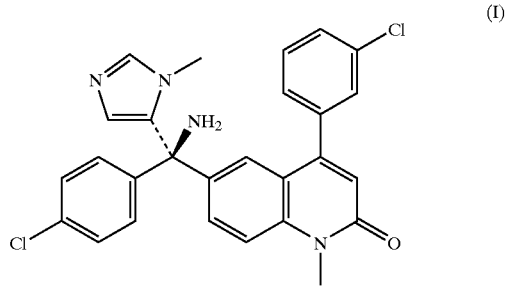

The preparation of R115777 is described in WO97/21701 by a synthetic route which includes the key step of introducing the 1-methyl imidazolyl group into a corresponding oxo compound as shown below:

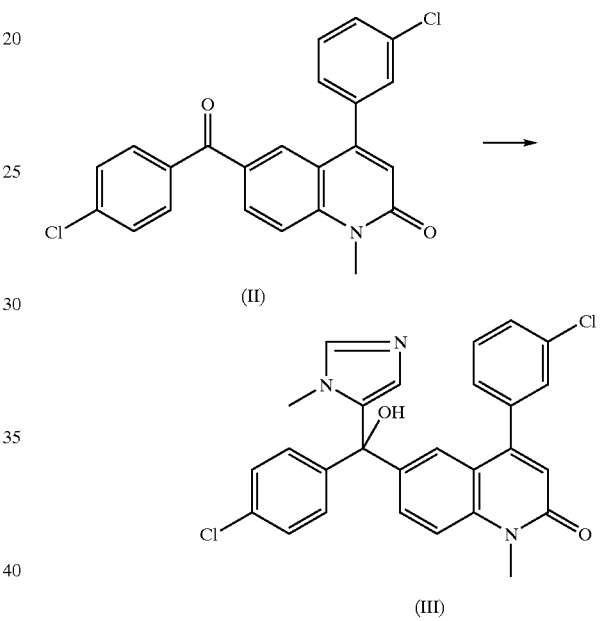

As described in Example B1 of the above patent specification, 1-methyl imidazole in tetrahydrofuran is mixed with a solution of n-butyllithium in a hexane solvent to which is added chlorotriethylsilane (triethylsilyl chloride), followed by a further addition of n-butyllithium in hexane, the resulting mixture being cooled to −78° C. before the addition of a solution of compound (II) in tetrahydrofuran. The reaction mixture is subsequently brought to room temperature, and then hydrolysed, extracted with ethyl acetate and the organic layer worked up to obtain the desired product resulting in a 52% yield of the compound (III). The latter compound can then be converted into R115777 as described in WO97/21701.

In order to ensure an economical supply of R115777 for development purposes and marketing, an efficient synthetic process for the production of R115777 is required. However, the procedure described in WO97/21701 above for converting compound (II) to compound (III) has a number of disadvantages. For example, the procedure results in the undesired formation of a corresponding compound in which the imidazole ring is attached to the remainder of the molecule at the 2-position of the ring instead of the desired 5-position in R115777. In order to obtain an economic production of the desired 5-isomer, it is important to reduce the formation of the undesired 2-isomer, and on a commercial scale, even such a reduction by say one or two percentage points represents an important desideratum. Also there is significant formation of other impurities in the final product, for example the corresponding bis-imidazole compound. The use of n-butyllithium is also undesirable in a commercial process in view of its pyrophoric nature and the formation of butane, a flammable gas, as the by-product. Finally, the carrying out of the process at a temperature as low as −78° C. is inconvenient and costly on a commercial scale in view of the specialised equipment required to perform a large scale process at such low temperature. There is therefore a need to improve the above reaction step whereby it can be carried out in an efficient and economical manner on a commercial scale.

It is an object of the present invention to provide a new and improved process for the preparation of the compound (III) from compound (II) in an improved yield of the former compound while minimising the formation of undesired isomers and under conditions which provide economic advantages for operation on a commercial scale. We have now found that such improvements in yield, impurity profile and commercial ease of operation can be achieved by the use of n-hexyllithium in place of n-butyllithium and the use of triisobutylsilyl chloride in place of triethylsilyl chloride, with particularly advantageous results obtained by the use of a temperature of at least −40° C.

According to one feature of the present invention therefore we provide a process for the preparation of a compound (III), i.e. 4-(3-chlorophenyl)-6-[(4-chlorophenyl)hydroxy(1-methyl-1H-imidazol-5-yl)methyl]-1-methyl-2(1H)-quinolinone, and its pharmaceutically acceptable salts:

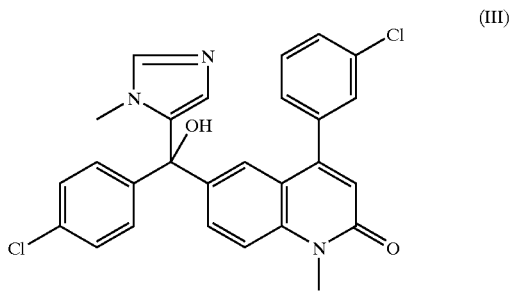

(III)

which comprises reacting a compound of formula (II), i.e. 6-(4-chlorobenzoyl)-4-(3-chlorophenyl)-1-methyl-2(1H)quinolinone:

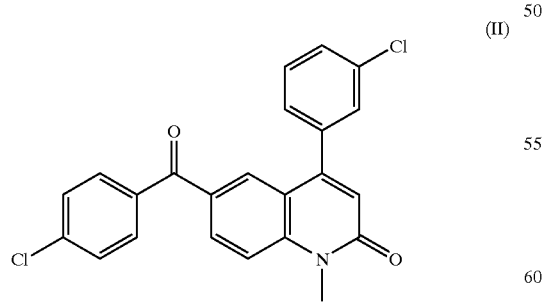

(II)

with a $C_{6-8}$alkyllithium compound, 1-methylimidazole and a tri($C_{4-6}$alkyl)silyl halide.

The $C_{6-8}$alkyllithium compound is preferably a hexyllithium especially n-hexyllithium. The tri($C_{4-6}$alkyl)silyl halide is preferably a tributylsilyl halide especially tri-iso-butylsilyl halide. The silyl halide is preferably a silyl chloride.

The above reaction is generally carried out at a temperature of at least −40° C., preferably at least −20° C., and preferably −5 to +5° C., especially about 0° C., the higher temperatures providing an improved C5-/C2-isomer ratio, i.e. the ratio between the compound in which the imidazolyl group is attached to the remainder of the molecule at the C5-position and the corresponding compound attached at the C2-position. This selectivity at such relatively high temperatures is remarkable in view of suggestions in the literature that the silyl group is unsuitable as a blocking group, due to the 2- to 5-position migration of 2-(trialkylsilyl)-substituted 5-lithio-1-methylimidazoles (G. Shapiro and M. Marzi, Tetrahedron Letters, Vol. 34, No. 21, pp 3401–3404, 1993; G. Shapiro and B. Gomez-Lor, J. Organic Chemistry, Vol. 59, pp 5524–5526, 1994).

The reaction is conveniently effected in an ethereal organic solvent, for example diethyl ether, tert-butyl methyl ether or more preferably tetrahydrofuran.

In more detail, the reaction may be conveniently effected by initially preparing a solution of 1-methylimidazole in a solvent such as tetrahydrofuran, to which is added a portion of the hexyllithium in a solvent such as n-hexane. The silyl halide is then added to the resulting reaction mixture, and a further portion of the hexyllithium in a solvent such as n-hexane is also added. The compound of formula (II) in a solvent such as tetrahydrofuran is then added to the reaction mixture, keeping the temperature between −5° C. and 0° C.

The resulting product of formula (III) can be conveniently isolated by crystallisation as a base, or by salt formation. After concentration of the reaction mixture, a suitable solvent, preferably iso-propyl acetate, is added to the residue and precipitation of the product results. For salt formation, hydrochloric acid gas, or hydrochloric acid solution in preferably 2-propanol, is added directly to the reaction mixture in tetrahydrofuran resulting in precipitation of the salt. Alternatively, hydrochloric acid is added to a solution of the reaction residue in a suitable solvent, preferably acetone, resulting in precipitation of the salt. The resulting compound of formula (III) can be subsequently converted into R115777 for example as described in WO97/21701, or more particularly as described below.

Thus, for example the compound of formula (III) can be chlorinated to form the following compound of formula (IV), i.e. 4-(3-chlorophenyl)-6-[chloro-(4-chlorophenyl)(1-methyl-1H-imidazol-5-yl)methyl]-1-methyl-2(1H)-quinolinone:

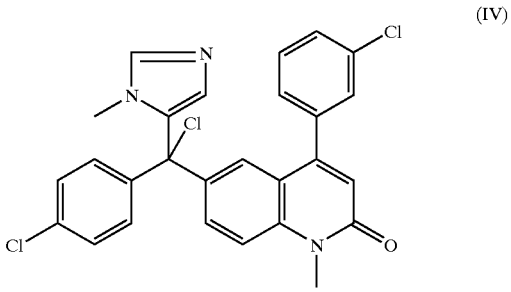

(IV)

The above chlorination reaction can be effected for example by treatment of the compound of formula (III) with thionyl chloride or phosphorus trichloride, in an inert solvent, e.g. toluene, N,N-dimethylacetamide or, more preferably, N,N-dimethylimidazolidinone, for example at a temperature of from 0° C. to the reflux temperature of the reaction mixture, preferably at room temperature. The chloro compound of formula (IV) can then be treated, conveniently in situ without the need to isolate the compound, with an aminating agent to form the following amino compound of formula (V), i.e. 6-[amino(4-chlorophenyl)(1-methyl-1H-imidazol-5-yl)methyl]-4-(3-chlorophenyl)-1-methyl-2(1-H)-quinolinone:

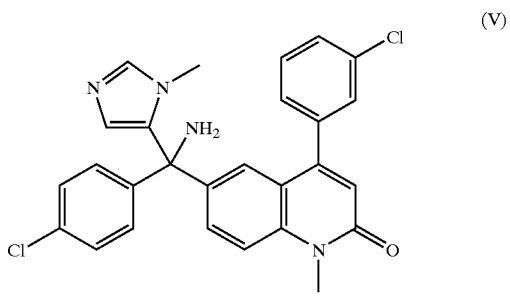

The amination reaction can be conveniently effected by treatment of the compound of formula (IV) with ammonia gas or a solution of ammonia in a suitable solvent, preferably methanol, the reaction being generally effected in an inert solvent e.g. toluene, or by the addition of ammonia to a solution of compound (IV) in N,N-dimethylacetamide or preferably N,N-dimethylimidazolidinone. The reaction is effected for example at a temperature of 0° to 40° C., preferably at room temperature. If the solvent is N,N-dimethylimidazolidinone, the resulting compound is isolated by the addition of water, resulting in precipitation of compound (V) which can then be filtered, washed with water and dried. The compound of formula (V) is obtained in an unresolved form and can be separated into its constituent enantiomers in conventional manner, for example by treatment with a chiral acid to form the respective diastereomeric salts which can then be separated and the salt having the desired R-configuration converted to the corresponding R115777 parent compound. Thus for example, the compound can be reacted with L-(−)-dibenzoyl tartaric acid (DBTA) to form the diastereomeric tartrate salt which is treated with a base, preferably aqueous ammonium hydroxide, to form the crude (R)-(+) R115777 which is then purified by recrystallisation from ethanol. The above intermediate tartrate salt, i.e. R-(−)-6-[amino(4-chlorophenyl)(1-methyl-1H-imidazol-5-yl)methyl]-4-(3-chlorophenyl)-1-methyl-2(1H)-quinolinone [R—(R*,R*)]-2,3-bis(benzoyloxy)butanedioate (2:3), is a new compound and represents a further feature of the invention. The resulting (R)-(+) R115777 can be used for the therapeutic treatment of cancers as described in WO 97/21701. The starting compound of formula (II), which is employed in the process according to the invention, can be prepared as described in WO 97/21701.

The following Examples illustrate the present invention.
Preparation of Compound (III):

110 ml of dry tetrahydrofuran was added to 7.6 ml of 1-methylimidazole (0.0946 mole) and the resulting solution cooled to −15° C. 37.8 ml of n-hexyllithium 2.5 M in n-hexane (0.0946 mole) was added, while the temperature during addition was kept between −5° C. and 0° C. After addition, the reaction mixture was stirred for 15 minutes, while cooling to −12° C. 26.2 ml of tri-iso-butylsilyl chloride (0.0964 mole) was added, while the temperature during addition was kept between −5° and 0° C. After addition, the reaction mixture was stirred for 15 minutes, while cooling to −13° C. 37.2 ml of n-hexyllithium 2.5 M in n-hexane (0.0930 mole) was added, while the temperature during addition was kept between −5° C. and 0° C. (some precipitation occured). After addition, the reaction mixture was stirred for 15 minutes, while cooling to −14° C. 128 ml of dry tetrahydrofuran was added to 26.22 g of 6-(4-chlorobenzoyl)-4-(3-chlorophenyl)-1-methyl-2(1H)-quinolinone (compound (II)) (0.0642 mole) and stirred until dissolution. This solution was added to the reaction mixture, while the temperature during addition was kept between −5° C. and 0° C. After addition, the reaction mixture was stirred for 15 minutes between −5° C. and 0° C. 128 ml of water was added to the reaction mixture, followed by the addition of 10.6 ml of acetic acid. The mixture was then heated to 40° C. and stirred for 2 hours. The layers were separated and the organic layer washed with 32 ml water. 64 ml water and 7.8 ml aqueous NaOH 50% were added to the organic layer which was stirred for 1 hour at ambient temperature. The layers were separated and the organic layer concentrated under reduced pressure, yielding 51.08 g of a brown oil (46.6 wt % 4-(3-chlorophenyl)-6-[(4-chlorophenyl)hydroxy(1-methyl-1H-imidazol-5-yl)methyl]-1-methyl-2(1H) quinolinone (compound III); 75.6% yield).

The product can be isolated via the procedures mentioned above. The resulting product was analysed by hplc using the following conditions:
Column: Hypersil C18-BD 3 μm, 100 mm×4 mm (i.d.)
Mobile phase:
Solvent A: 0.5% NH$_4$OAc
Solvent B: CH$_3$CN

| | Gradient: | |
| Time | % A | % B |
| --- | --- | --- |
| 0 | 100 | 0 |
| 15 | 0 | 100 |
| 18 | 0 | 100 |
| 19 | 100 | 0 |
| 23 | 100 | 0 |

Detector: UV 254 nm
Solvent: DMF

The product was found to have a C5:C2 ratio of 99.8:0.2. In contrast using n-butyllithium in place of n-hexyllithium, triethylsilyl chloride in place of tri-iso-butylsilyl chloride and conducting the process at −70° C., i.e. generally in accordance with prior art procedures discussed above, the resulting product had a C5:C2 ratio of 95:5, a significant difference in commercial terms.

Preparation of Compound (IV)

A 1 liter reaction vessel was charged with 105.4 g of 4-(3-chlorophenyl)-6-[(4-chlorophenyl)hydroxy(1-methyl-1H-imidazol-5-yl)methyl]-1-methyl-2(1H)-quinolinone hydrochloric acid salt (compound (III) and 400 ml of N,N-dimethylimidazolidinone added at 22° C. The mixture was stirred vigorously for 15 minutes at 22° C. and became homogeneous. 32.1 ml of thionyl chloride was added over 10 minutes to the reaction mixture, the reaction temperature rising from 22° C. to 40° C. After addition of the thionyl chloride, the reaction mixture was cooled from 40° C. to 22° C. and stirred for three hours at the latter temperature to provide a solution of 4-(3-chlorophenyl)-6-[chloro-(4-chlorophenyl)(1-methyl-1H-imidazol-5-yl)methyl]-1-methyl-2(1H)-quinolinone (compound (IV).

Preparation of Unresolved Compound (I)

429 ml of ammonia in methanol 7N was cooled to 5° C. in a 3 liter reaction vessel and the solution of compound (IV), obtained in the previous stage, added, while stirring, over 10 minutes, with an exothermic reaction, the temperature rising from 5° C. to 37° C. After the addition was complete, the reaction mixture was cooled to 22° C. and stirred for 20 hours. 1000 ml of water was then added over 20 minutes, the addition being slightly exothermic so the reaction mixture was cooled to keep the temperature below 30° C. The mixture was then stirred for 22 hours at 22° C., the resulting precipitate filtered off and the precipitate washed three times with 100 ml of water to provide a yield of 70–75% of 6-[amino(4-chlorophenyl)-1-methyl-1H-imidazol-5-ylmethyl]-4-(3-chlorophenyl)-1-methyl-2(1H)-quinolinone.

Resolution of Compound (I)

a) A 3 liter reaction vessel was charged with 146.8 g of 6-[amino(4-chlorophenyl)(1-methyl-1H-imidazol-5-yl)methyl]-4-(3-chlorophenyl)-1-methyl-2(1H)-quinolinone and 301.1 g of L-(−)-dibenzoyl-tartaric acid monohydrate, 1200 ml of acetone was added and the reaction mixture stirred vigorously for 10 minutes at 22° C. to form a solution which was seeded with 100 mg of the final tartrate salt product (obtained from previous screening experiments) and then stirred for 22 hours at 22° C. The resulting precipitate was filtered off and the precipitate was washed twice with 75 ml of acetone and the product dried at 50° C. in vacuo to yield 114.7 g of R-(−)-6-[amino(4-chlorophenyl)(1-methyl-1H-imidazol-5-yl)methyl]-4-(3-chlorophenyl)-1-methyl-2(1H)-quinolinone [R—(R*,R*)]-2,3-bis(benzoyloxy)butanedioate (2:3).

b) 41.08 g of the product of stage a) and 80 ml ethanol were stirred for 15 minutes at 22° C. 12.0 ml concentrated aqueous ammonium hydroxide was added over 2 minutes, and the reaction mixture stirred for 1 hour at 25° C. 160 ml water was added over 10 minutes at 25° C. and the mixture heated to reflux and stirred at reflux for 1 hour. The reaction mixture was then cooled to 20° C. and stirred for 16 hours at 20° C. The product was filtered, washed twice with 8 ml water and dried at 50° C. in vacuo to yield 16.87 g of (R)-(+)-6-[amino(4-chloro-phenyl)(1-methyl-1H-imidazol-5-yl)methyl]-4-(3-chlorophenyl)-1-methyl-2(1H)-quinolinone (compound (I)).

Purification of Compound (I)

265 ml of ethanol was added to 19.9 g of compound (I), obtained as described in the previous stage, and the mixture warmed while stirring to reflux temperature (78° C.) and then stirred at reflux temperature for 15 minutes before cooling the solution to 75° C. 1.0 g of activated carbon (Norit A Supra) was then added to the mixture which was stirred at reflux temperature for 1 hour, filtered while warm and the filter then washed with 20 ml warm ethanol. The filtrate and wash solvent were combined (the product spontaneously crystallizes at 48° C.), and the mixture warmed to reflux temperature and concentrated by removing 203 ml of ethanol. The resulting suspension was cooled to 22° C., stirred for 18 hours at 22° C., cooled to 2° C. and stirred for 5 more hours at 2° C. The precipitate was filtered and washed with 4 ml ethanol and the product dried at 50° C. in vacuo to yield 17.25 g of purified compound (I) which complies with the infrared spectrum of reference material.

What is claimed is:

1. A process for the preparation of 4-(3-chlorophenyl)-6-[(4-chlorophenyl)hydroxy(1-methyl-1H-imidazol-5-yl)methyl]-1-methyl-2(1H)-quinolinone (III) and its pharmaceutically acceptable salts:

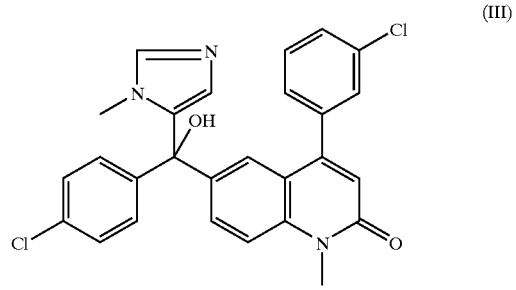

which comprises reacting 6-(4-chlorobenzoyl)-4-(3-chlorophenyl)-1-methyl-2(1H)-quinolinone (II):

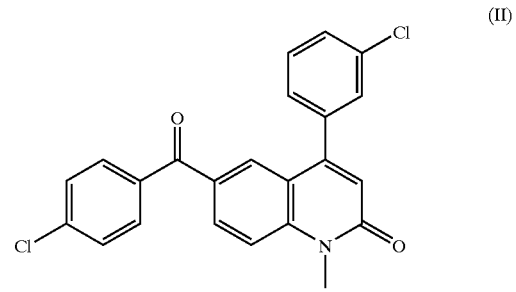

with a $C_{6-8}$alkyllithium compound, 1-methylimidazole and a tri($C_{4-6}$alkyl)silyl halide.

2. A process as claimed in claim 1 in which the $C_{6-8}$alkyllithium compound is a hexyllithium compound.

3. A process as claimed in claim 2 in which the hexyllithium compound is n-hexyllithium.

4. A process as claimed in claim 1 in which the tri($C_{4-6}$alkyl)silyl halide is a tributylsilyl halide.

5. A process as claimed in claim 4 in which the tributylsilyl halide is a tri-iso-butylsilyl halide.

6. A process as claimed in claim 1 in which the tri($C_{4-6}$alkyl)silyl halide is a tri($C_{4-6}$alkyl)silyl chloride.

7. A process as claimed in claim 1 in which the reaction is effected at a temperature of at least −40° C.

8. A process as claimed in claim 7 in which the reaction is effected at a temperature of at least −20° C.

9. A process as claimed in claim 8 in which the reaction is effected at a temperature of −5 to +5° C.

10. A process as claimed in claim 1 in which the resulting compound (III) is subsequently used as intermediate for the preparation of (R)-(+)-6-[amino(4-chloro-phenyl)(1-methyl-1H-imidazol-5-yl)methyl]-4-(3-chlorophenyl)-1-methyl-2(1H)-quinolinone.

* * * * *